United States Patent
Inagaki et al.

(10) Patent No.: US 7,568,801 B2
(45) Date of Patent: Aug. 4, 2009

(54) OPTOTYPE PRESENTING APPARATUS

(75) Inventors: Yoshiyuki Inagaki, Toyokawa (JP);
Yoshinobu Hosoi, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 12/081,009

(22) Filed: Apr. 9, 2008

(65) Prior Publication Data
US 2008/0259277 A1 Oct. 23, 2008

(30) Foreign Application Priority Data
Apr. 20, 2007 (JP) .............................. 2007-112339

(51) Int. Cl.
*A61B 3/02* (2006.01)
(52) U.S. Cl. .................... 351/239; 351/232; 351/242
(58) Field of Classification Search ................ 351/232, 351/239, 240, 242, 243
See application file for complete search history.

(56) References Cited

U.S. PATENT DOCUMENTS

| 4,415,243 | A | | 11/1983 | Gottlob et al. |
| 5,436,681 | A | | 7/1995 | Michaels |
| 5,629,748 | A | * | 5/1997 | Hayashi et al. ............. 351/232 |
| 5,638,082 | A | | 6/1997 | Grimm |
| 5,997,142 | A | | 12/1999 | Nakagawa |
| 7,216,984 | B2 | * | 5/2007 | Hosoi ......................... 351/237 |
| 2008/0204662 | A1 | * | 8/2008 | Kanazawa et al. .......... 351/243 |

FOREIGN PATENT DOCUMENTS

| EP | 0 060 986 A1 | 9/1982 |
| EP | 0 595 023 A1 | 5/1994 |
| EP | 0 966 916 A1 | 12/1999 |
| JP | A-5-253186 | 10/1993 |
| JP | A-7-322304 | 12/1995 |
| JP | A-2002-185983 | 6/2002 |
| JP | A-2002-311385 | 10/2002 |
| JP | A-2004-170693 | 6/2004 |
| JP | A-2006-42978 | 2/2006 |

* cited by examiner

*Primary Examiner*—Huy K Mai
(74) *Attorney, Agent, or Firm*—Oliff & Berridge, PLC (57) ABSTRACT

An optotype presenting apparatus of a display type with which a polarization red-green test with accuracy can be performed has a display, a polarization optical member including first and second optical regions changing light from the display into light having perpendicular polarizing axes, a selector, regions where optotypes for left and right eyes are to be presented, and a controller, wherein, when a polarization red-green test chart is selected with the selector, the controller controls the display to display a left-eye polarization red-green optotype in pixel regions corresponding to the first regions within the left-optotype-presenting region and display pixel regions in white corresponding to the second regions within the left-optotype-presenting region, while the controller controls to display a right-eye polarization red-green optotype in pixel regions corresponding to the second regions within the right-optotype-presenting region and display pixel regions in white corresponding to the first regions within the right-optotype-presenting region.

6 Claims, 7 Drawing Sheets

OPTOTYPE PRESENTING APPARATUS

BACKGROUND OF THE INVENTION

1. Field of the Invention

The present invention relates to an optotype presenting apparatus which presents an optotype and/or a test chart for testing visual performance of an eye.

2. Description of Related Art

Conventionally, there is known an optotype presenting apparatus of a projection type such that an optotype and/or a test chart drawn on a chart disk is illuminated from behind so as to be enlarged and projected onto a screen at a distance for a test. In addition, there is known an optotype presenting apparatus of a display type such that an optotype and/or a test chart is shown on a display (see Japanese Patent Application Unexamined Publication No. 2006-42978).

In an optotype presenting apparatus of a display type, a technique for displaying a three-dimensional image can be used in order to present different optotypes to a right eye and a left eye of an examinee (see U.S. Pat. No. 5,638,082 corresponding to Japanese Patent Application Unexamined Publication No. Hei07-322304, and Japanese Patent Application Unexamined Publication No. 2002-311385). To be more specific, the different optotypes are presented to the right eye and the left eye by placing in front of the display a sheet-like polarization optical member which has two types of optical regions alternately arranged in a linear pattern or a grid pattern based on the size of pixels of the display and changes thereby light exiting from the display into light having polarizing axes perpendicular to each other when transmitting the light and by placing in front of the right eye and the left eye different polarization filters which have polarizing axes perpendicular to each other and coinciding with the polarizing axes of the light transmitted by the polarization optical member, allowing a binocular vision test to be performed.

Incidentally, as an example of a test chart used for the binocular vision test, a polarization red-green test chart is cited which is used for checking binocular balance and whether corrected refractive power is undercorrection or overcorrection (see Japanese Patent Application Unexamined Publication No. Hei05-253186).

Figure 7A:
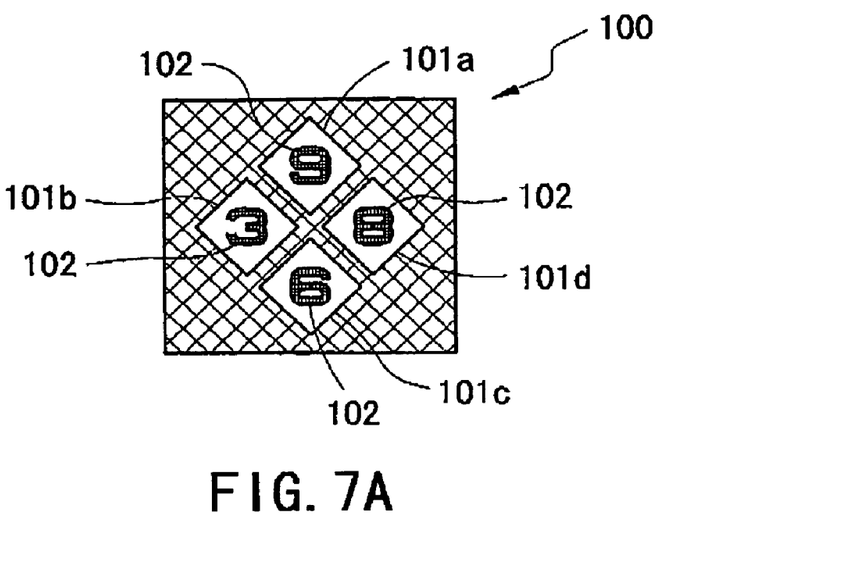
FIGS. 7A and 7C are views for illustrating another arrangement of the optotypes on the polarization red-green test chart.
Figure 7B:
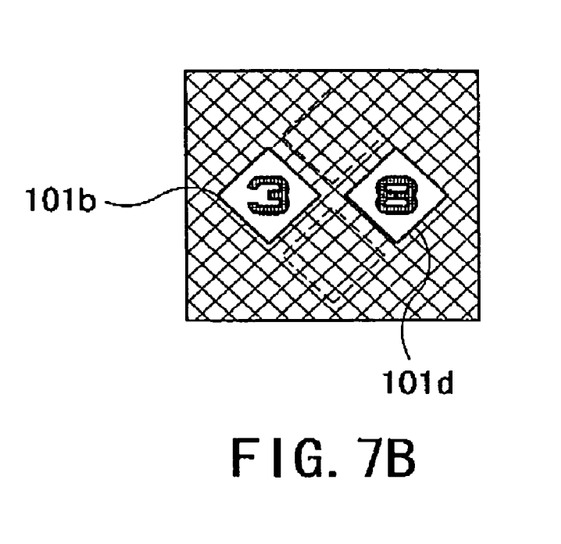
Figure 7C:
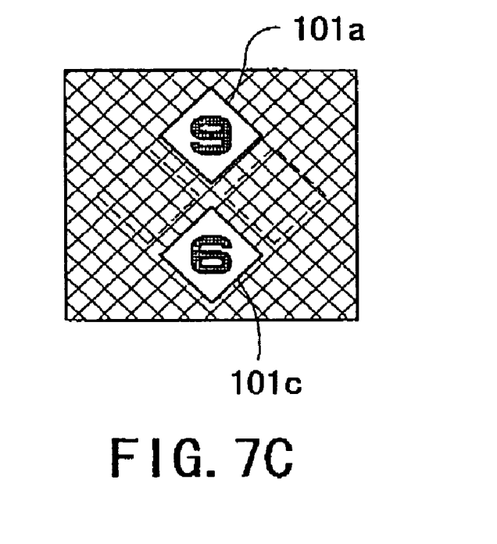

FIGS. 7A to 7C are views showing one example of a polarization red-green test chart 100 which is used in the conventional optotype presenting apparatus of the projection type. In FIG. 7A, an optotype 101a at an upper portion and an optotype 101b at a left portion are green optotypes, and an optotype 101c at a lower portion and an optotype 101d at a right portion are red optotypes. Inside the optotypes 101a to 101d, black characters 102 are drawn. At the time of the test, different polarization filters having polarizing axes perpendicular to each other are placed in front of a right eye and a left eye of an examinee in order to enable a binocular balance test to be concurrently performed. In addition, in the conventional optotype presenting apparatus of the projection type, a polarization filter which has a polarizing axis coinciding with the polarizing axis of the polarization filter for the left eye is placed on a chart disk so that the optotypes 101b and 101d are visually perceived against a black background by the left eye as shown in FIG. 7B. Meanwhile, a polarization filter which has a polarizing axis coinciding with the polarizing axis of the polarization filter for the right eye is placed on the chart disk so that the optotypes 101a and 101c are visually perceived against a black background by the right eye as shown in FIG. 7C. When the examinee looks at the test chart 100 by both eyes, the optotypes 101a to 101d are visually perceived compositely against a black background as shown in FIG. 7A.

Then, by checking which of the character 102 on the green optotypes or the character 102 on the red optotypes is more clearly visible, it is determined whether the corrected refractive power is overcorrection or undercorrection, and the binocular balance is concurrently checked.

Meanwhile, presentation of the polarization red-green test chart is performed by the conventional optotype presenting apparatus of the display type as follows.

By using a polarization element (vectograph film) having polarizing axes perpendicular to each other (see U.S. Pat. No. 5,638,082 corresponding to Japanese Patent Application Unexamined Publication No. Hei07-322304), or using a wave plate in addition to a polarization plate placed in front of a display (see Japanese Patent Application Unexamined Publication No. 2002-311385), the display of two types of the optical regions alternately arranged in the linear pattern based on the size of the pixels of the display is made so that some pixels of the display are displayed in black, the pixels corresponding to the optical regions not intended to be visually perceived by either of the eyes in a similar manner that the optotypes 101a to 101d are visually perceived against the black background as described above referring to FIGS. 7A to 7C. At this time, there is a gap between a light-emitting element of the display and the polarization optical member, so that a slight leak of light occurs while an attempt is carried out to present the different optotypes to the right eye and the left eye. To be more specific, because light through the optotypes 101a and 101c to be presented to the right eye leaks out, the optotypes 101a and 101c are visually perceived faintly in addition to the optotypes 101b and 101d to be presented to the left eye which are shown in FIG. 7B. Similarly, because light through the optotypes 101b and 101d to be presented to the left eye leaks out, the optotypes 101b and 101d are visually perceived faintly in addition to the optotypes 101a and 101c to be presented to the right eye which are shown in FIG. 7C. Because of this, a polarization red-green test with accuracy cannot be performed.

SUMMARY OF THE INVENTION

An object of the invention is to provide an optotype presenting apparatus of a display type with which a polarization red-green test with accuracy can be performed.

To achieve the objects and in accordance with the purpose of the present invention, an optotype presenting apparatus which presents an optotype and a test chart used for testing visual performance, the apparatus comprising a display, a polarization optical member placed in front of the display which includes first optical regions and second optical regions which are alternately arranged in either one of a linear pattern and a grid pattern based on the size of pixels of the display, the first optical regions changing light exiting from the display into light having a polarizing axis, the second optical regions changing light exiting from the display into light having a polarizing axis, the polarizing axes being perpendicular to each other, a selector which comprises a switch with which a test chart for a binocular visual test including a polarization red-green test chart is selected, a region where an optotype for a left eye is to be presented and a region where an optotype for a right eye is to be presented, the regions being provided on a display surface of the display, and a controller which controls display of the display, wherein, when the polarization red-green test chart is selected with the selector, the controller controls the display to display a polarization red-green optotype for a left eye in pixel regions which correspond to the first optical regions and are within the region where the optotype for the left eye is to be presented, and controls the display to display pixel regions in white which correspond to the second optical regions and are within the region where the optotype for the left eye is to be presented, while the controller controls the display to display a polarization red-green optotype for a right eye in pixel regions which correspond to the second optical regions and are within the region where the optotype for the right eye is to be presented, and controls the display to display pixel regions in white which correspond to the first optical regions and are within the region where the optotype for the right eye is to be presented.

Additional objects and advantages of the invention are set forth in the description which follows, are obvious from the description, or may be learned by practicing the invention. The objects and advantages of the invention may be realized and attained by the optotype presenting apparatus in the claims.

BRIEF DESCRIPTION OF THE DRAWINGS

The accompanying drawings, which are incorporated in and constitute a part of this specification, illustrate embodiment of the present invention and, together with the description, serve to explain the objects, advantages and principles of the invention. In the drawings.

DETAILED DESCRIPTION OF THE PREFERRED EMBODIMENTS

Figure 1:
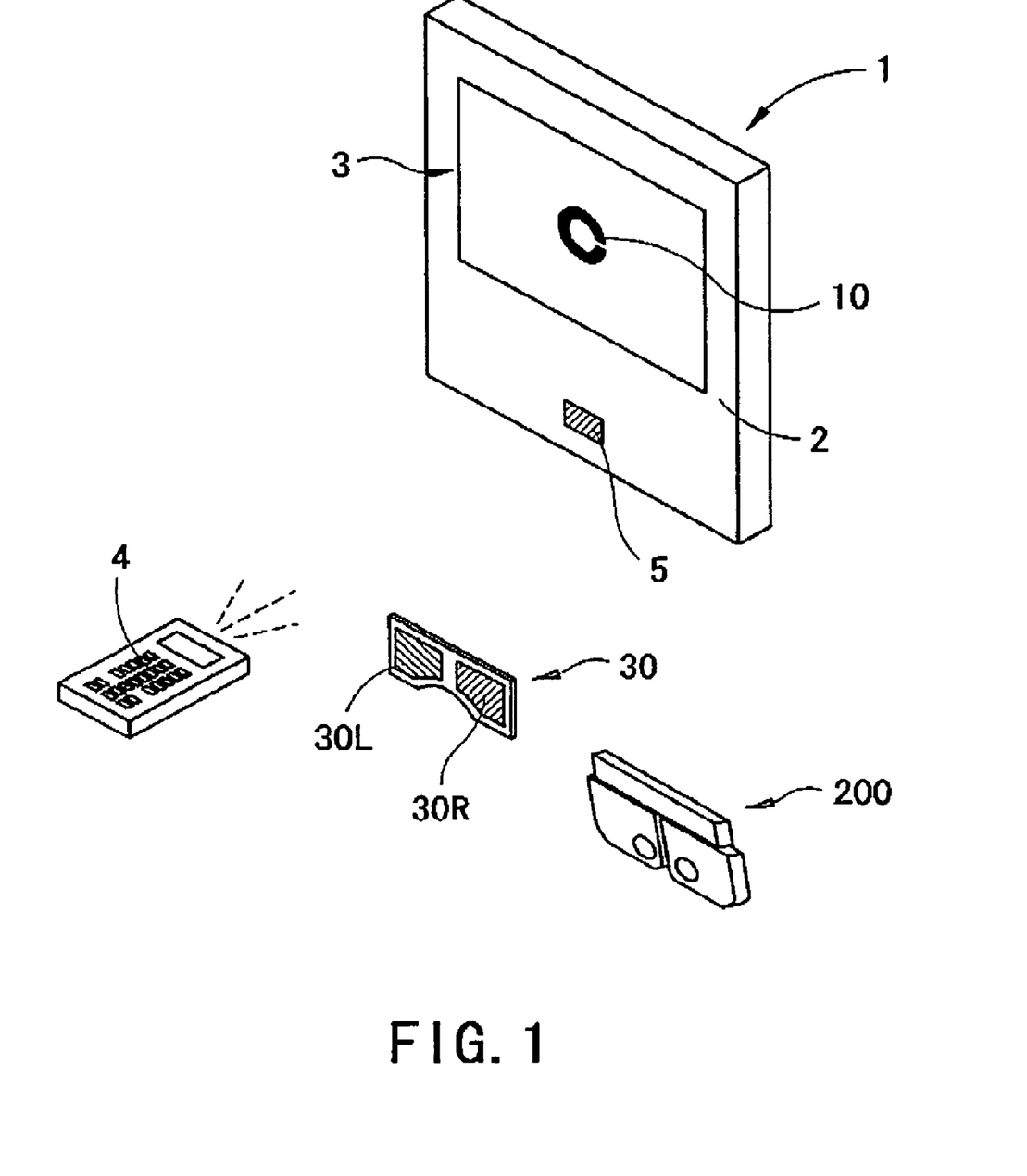
FIG. 1 is an external schematic view showing an optotype presenting apparatus according to a preferred embodiment of the present invention.

A description of one preferred embodiment of an optotype presenting apparatus embodied by the present invention will be provided below with reference to the accompanying drawings. FIG. 1 is an external schematic view showing an optotype presenting apparatus according to a preferred embodiment of the present invention.

An optotype presenting apparatus 1 comprises a housing 2, and a presenting unit 3 arranged to present an optotype which is placed on a front surface of the housing 2 (detailed descriptions of the presenting unit 3 will be provided later). The presenting unit 3 is capable of presenting an optotype 10 including an optotype of a given size for a visual acuity test, and a test chart for a binocular vision test such as a polarization red-green test chart even when the optotype presenting apparatus 1 is placed at a far distance for the test, e.g., a distance of five meters. The housing 2 is shaped thinly so as to be used on a wall.

At a lower portion on the front surface of the housing 2, a receiving portion 5 is provided, which receives a communication signal as infrared light from a remote control (selector) 4. The optotype 10 to be presented by the presenting unit 3 is changed by operating the remote control 4. In addition, when an optotype for a visual acuity test which consists of one character is presented as the optotype 10, the optotype 10 is displayed at a center portion of the presenting unit 3. Polarization spectacles 30 including a polarization filter 30L and a polarization filter 30R which have polarizing axes perpendicular to each other are used for the binocular vision test. The polarization filter 30L for a left eye has the polarizing axis oriented in the direction of 135 degrees, and the polarization filter 30R for a right eye has the polarizing axis oriented in the direction of 45 degrees. If a subjective eye refractive power measurement apparatus (phoropter) 200 in which corrective lenses such as spherical lenses are switched to be placed in right and left test windows is used in order to check corrected refractive power, polarization filters having polarizing axes perpendicular to each other which are similar to the polarization filters provided to the polarization spectacles 30 are switched and placed in the right and left test windows at the time of the binocular vision test.

Figure 2:
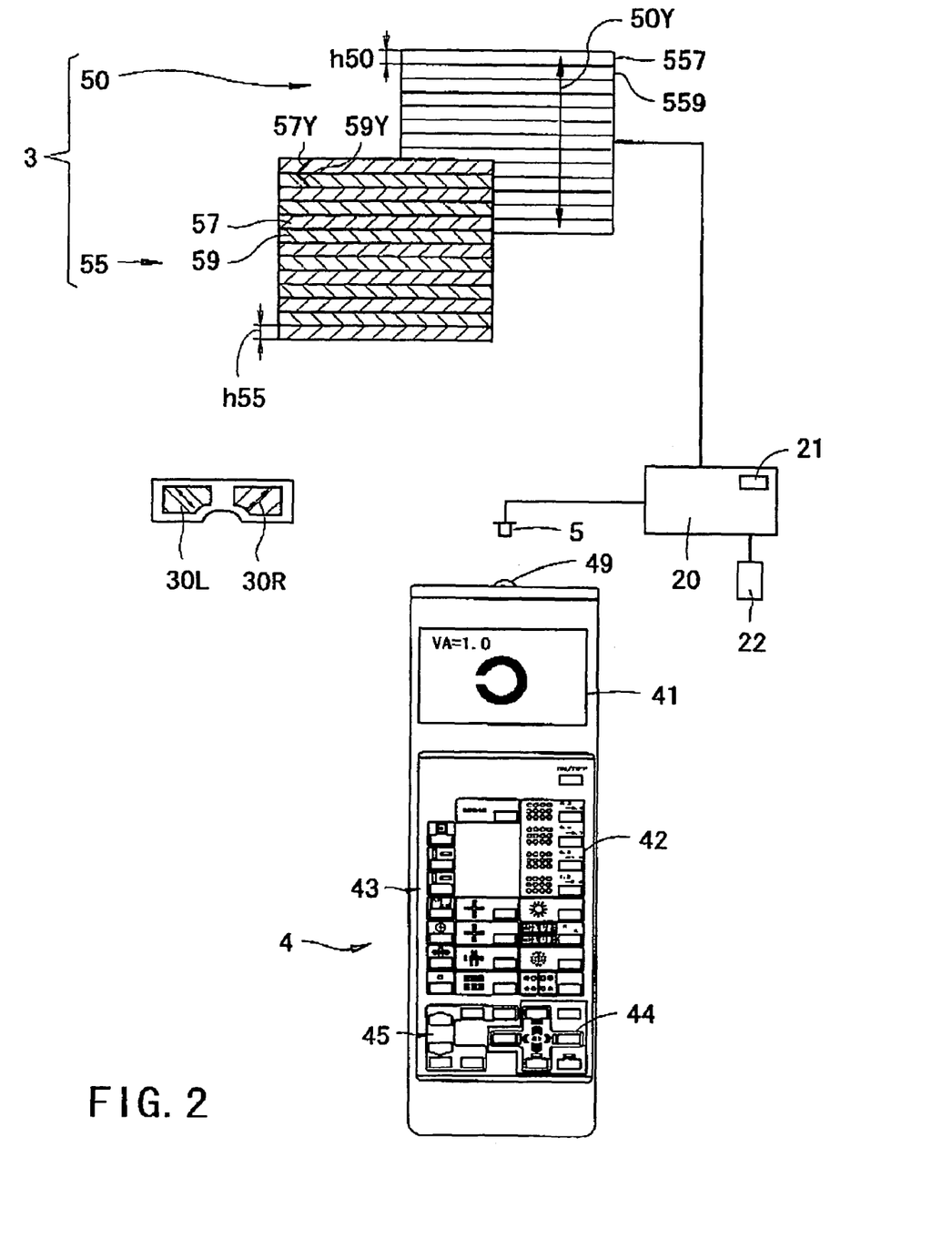
FIG. 2 is a control block diagram of the optotype presenting apparatus.

FIG. 2 is a control block diagram of the optotype presenting apparatus 1. A color liquid crystal display (LCD) 50 included in the presenting unit 3, and the receiving portion 5 are connected to a control unit (controller) 20. The control unit 20 comprises a memory 21 which stores various types of optotypes and test charts, a decoder circuit which decodes the command signal from the remote control 4, and other constituent elements. When a signal for switching the optotypes or the test charts, or other signals from the remote control 4 is inputted to the control unit 20, the control unit 20 performs display controls of the display 50.

The remote control 4 comprises a plurality of switches for selecting the optotypes and the test charts to be displayed on the display 50, and a liquid crystal display 41 which displays a status of the operation by the switches. A switch group 42 for switching the optotypes for the visual acuity test includes switches corresponding to visual acuity values of the optotypes, and when the switch corresponding to one visual acuity value is pushed, an optotype for that visual acuity is selected and displayed on the display 50. At this time, the same optotype is displayed also on the display 41 together with the visual acuity value. A switch group 43 for switching the test charts other than the optotypes for the visual acuity test includes switches for selecting and displaying the test chart including the polarization red-green test chart which is used for testing various kinds of visual performance of the eye in the binocular visual test. Switches 44 for orientation change are arranged to change the orientation of a gap of a Landort-ring optotype which is the optotype for the visual acuity test. Switches 45 are arranged to raise and lower the visual acuity value of the optotype for the visual acuity test which is displayed on the presenting unit 3. A transmitting portion 49 transmits the command signal as the infrared light.

Next, the configuration of the presenting unit 3 is described. The presenting unit 3 comprises the display 50, and a sheet-like polarization optical member 55 which is placed to cover at least an optotype presenting area of the display 50. The display 50 comprises a polarization plate, so that linearly polarized light having a polarizing axis in a predetermined direction (a vertical direction, a horizontal direction, or an oblique direction of 45 degrees) is emitted from the display 50. In the preferred embodiment of the present invention, light having a polarizing axis (polarization plane) in the vertical direction indicated by an arrow 50Y is emitted. The polarization optical member 55 has two types of optical regions 57 and 59 alternately arranged in a linear pattern or a grid pattern based on the size of pixels of the display 50, and changes the linearly polarized light from the display 50 into linearly polarized light having polarizing axes perpendicular to each other when transmitting the light. In the preferred embodiment of the present invention, the polarization optical member 55 is made of half wavelength plates which have a function of making a phase difference.

As is well known, a half wavelength plate is arranged to rotate a vibration direction of incident light by 2×θ degree(s) when the incident light with a polarization plane enters at θ degree(s) with respect to a fast axis (or a slow axis) of the half wavelength plate. In other words, the half wavelength plate has a function of rotating a direction of the polarizing axis (vibration direction) of the incident light by inclining a direction of its optically principal axis that is the fast axis (or the slow axis) with respect to the polarizing axis direction of the incident light, and has a property of being capable of maintaining light intensity of the incident light.

In FIG. 2, the half wavelength plates of the optical regions 57 in the linear pattern define optical regions for a right eye, and the direction of the optically principal axis of the half wavelength plates is arranged so that the incident light is changed into light having a polarizing axis direction (direction indicated by an arrow 57Y) which coincides with a polarizing axis direction of 45 degrees of the polarization filter 30R for the right eye of the polarization spectacles 30. In addition, the half wavelength plates of the optical regions 59 in the linear pattern define optical regions for a left eye, and the direction of the optically principal axis of the half wavelength plates is arranged so that the incident light is changed into light having a polarizing axis direction (direction indicated by a narrow 59Y) which coincides with a polarizing axis direction of 135 degrees of the polarization filter 30L for the left eye of the polarization spectacles 30. The polarizing axis directions of the light for the right eye and the left eye may be changed to each other, which are not limited to the preferred embodiment of the present invention. When looking at the display on the presenting unit 3 through the polarization filters 30R and 30L placed in front of the right and left eyes, the examinee visually perceives by the left eye only the light from the optical regions 59 which is capable of passing through the polarization filter 30L, while the light from the optical regions 57 is blocked by the polarization filter 30L and is not visually perceived by the left eye. In contrast, the examinee visually perceives by the right eye only the light from the optical regions 57 which is capable of passing through the polarization filter 30R, while the light from the optical regions 59 is blocked by the polarization filter 30R and is not visually perceived by the right eye. Therefore, different optotypes can be presented to the right eye and the left eye.

Incidentally, if the display 50 is arranged to emit light having a polarizing axis direction of 45 degrees, it is enough that an optical member which does not have a function of making a phase difference (i.e., an optical member which is not made of half wavelength plates) and is capable of transmitting the light maintaining the polarizing axis direction of 45 degrees is used instead of the polarization optical member 55.

In addition, in FIG. 2, display regions 557 of the display 50 correspond to the optical regions 57, and display regions 559 of the display 50 correspond to the optical regions 59. Each of the display regions 557 and 559 corresponds to one lateral line of pixels of the display 50. If the optical regions 57 and 59 are as small as not to be distinguished from each other with the examinee's eyes at the distance for the test, it is also preferable that the optical regions 57 and 59 are arranged to cover a region of an integral multiple of one lateral line of pixels of the display 50. A length h50 in a vertical direction of one lateral line of pixels of the display 50 is, for example, about 0.26 mm. A length h55 in a vertical direction of the optical regions 57 and 59 is almost equal to the length h50. In the preferred embodiment of the present invention, the optical regions 57 and 59 and the corresponding display regions 557 and 559 of the display 50 are arranged in a laterally linear pattern. However, it is also preferable that they are arranged in a vertically linear pattern. In addition, it is also preferable that two types of the optical regions 57 and 59 may be arranged in a grid pattern.

In the preferred embodiment of the present invention, a liquid crystal display is used as the display 50. However, a plasma display, an organic EL display, an SED display and other displays can be also preferably used as the display 50. If light exiting from the displays other than the liquid crystal display does not have a property of linearly polarized light, half wavelength plates having a function of making a phase difference can be preferably used as the polarization optical member 55 by placing a polarization plate between the display 50 and the polarization optical member 55.

Incidentally, it is also preferable that the polarization optical member 55 has the optical regions 57 which are made of polarization plates having a polarizing axis direction of 45 degrees and the optical regions 59 which are made of polarization plates having a polarizing axis direction of 135 degrees as described in U.S. Pat. No. 5,638,082. When the displays other than the liquid crystal display are used, a polarization plate may be used as the polarization optical member 55 as described in U.S. Pat. No. 5,638,082.

Figure 3A:
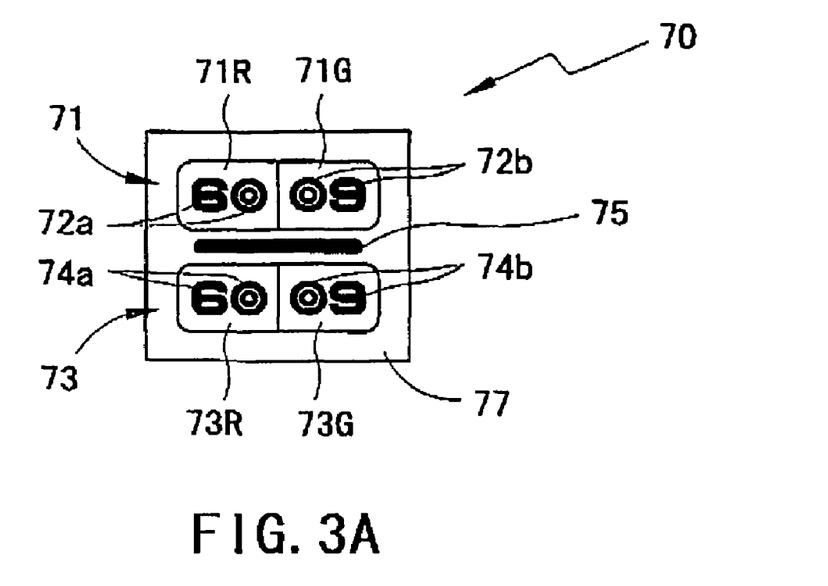
FIGS. 3A to 3C are views for illustrating a polarization red-green test chart used in the optotype presenting apparatus.

Next, a description of the polarization red-green test chart will be provided. FIG. 3A is a view showing an example of the polarization red-green test chart to be presented by the presenting unit 3. A polarization red-green test chart 70 shown in FIG. 3A includes a polarization red-green optotype 71 for a right eye (hereinafter referred to as a right polarization R/G optotype) which is visually perceived only by the right eye, a polarization red-green optotype 73 for a left eye (hereinafter referred to as a left polarization R/G optotype) which is visually perceived only by the left eye, and a fusion optotype 75 in black which is visually perceived by both eyes. The fusion optotype 75 is placed between the right polarization R/G optotype 71 and the left polarization R/G optotype 73.

In addition, the right polarization R/G optotype 71 which is placed in an upper portion of the polarization red-green test chart 70 includes a red optotype 71R placed on the left side and a green optotype 71G placed on the right side. The red optotype 71R is a red region in which black characters 72a are placed. The green optotype 71G is a green region in which black characters 72b are placed. Similarly to the right polarization R/G optotype 71, the left polarization R/G optotype 73 which is placed in a lower portion of the polarization red-green test chart 70 includes a red optotype 73R placed on the left side and a green optotype 73G placed on the right side. The red optotype 73R is a red region in which black characters 74a are placed. The green optotype 73G is a green region in which black characters 74b are placed.

The polarization red-green test chart 70 is arranged such that the right polarization R/G optotype 71 placed in the upper portion and the fusion optotype 75 placed in the middle portion are presented to the right eye through the polarization filter 30R, and the left polarization R/G optotype 73 placed in the lower portion and the fusion optotype 75 placed in the middle portion are presented to the left eye through the polarization filter 30L. When the examinee looks at the polarization red-green test chart 70 with both eyes, an image of the fusion optotype 75 presented to the left eye and an image of the fusion optotype 75 presented to the right eye, which have the same shape and the same color, fuse into one image 30 as to be visually perceived as an integrated optotype as shown in FIG. 3A. By checking which is more clearly visible, the black characters 72a in the red optotype 71R or the black characters 72b in the green optotype 71G in the right polarization R/G optotype 71 presented to the right eye, whether corrected refractive power of the right eye is undercorrection or overcorrection is tested. Similarly, by checking which is more clearly visible, the black characters 74a in the red optotype 73R or the black characters 74b in the green optotype 73G in the left polarization R/G optotype 73 presented to the left eye, whether corrected refractive power of the left eye is undercorrection or overcorrection is tested. At the same time, balance between the right and left eyes in a corrected state is tested by making the examinee visually compare the black characters 72a and 72b in the right polarization R/G optotype 71 and the black characters 74a and 74b in the left polarization R/G optotype 73.

Figure 3B:
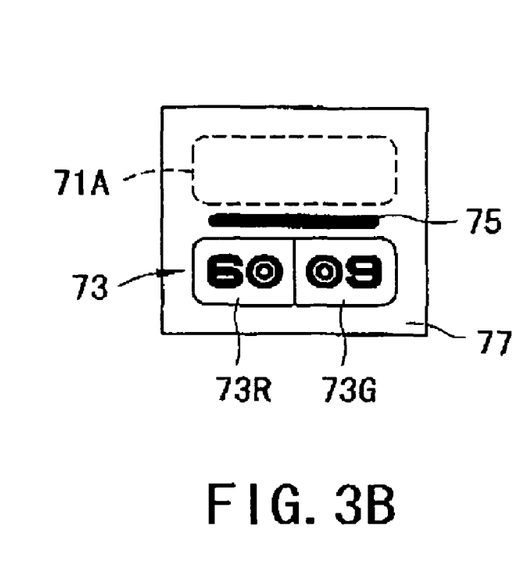
Figure 3C:
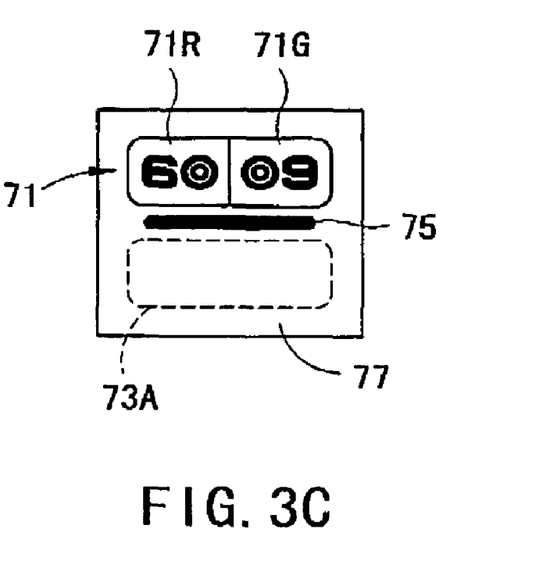

Here, a description of a case where a polarization red-green test chart as described above is used in a conventional optotype presenting apparatus of a projection type will be provided. In such a case, a background region of the right polarization R/G optotype 71 and the left polarization R/G optotype 73 is necessarily made black. In the optotype presenting apparatus of the projection type, one optotype is prepared in a region having a diameter of 10 mm on a chart disk. Red filters are provided on red regions (71R and 73R), and green filters are provided on green regions (71G and 73G). Further, a polarization filter which has a polarizing axis coinciding with the polarizing axis of the polarization filter 30R for the right eye is provided on the region of the right polarization R/G optotype 71, and a polarization filter which has a polarizing axis coinciding with the polarizing axis of the polarization filter 30L for the left eye is provided on the region of the left polarization R/G optotype 73. In this case, a region 71A where the right polarization R/G optotype 71 is provided (the region indicated by the dashed lines in FIG. 3B) is visually perceived in black as shown in FIG. 3B when the examinee looks at the polarization red-green test chart through the polarization filter 30L for the left eye because the polarizing axis of the polarization filter 30L for the left eye and the polarizing axis of the light transmitted through the right polarization R/G optotype 71 are perpendicular to each other. Based on the same principle, a region 73A where the left polarization R/G optotype 73 is provided is visually perceived in black as shown in FIG. 3C when the examinee looks at the polarization red-green test chart through the polarization filter 30R for the right eye. For this reason, the polarization red-green test chart is arranged so that a background region 77 of the right polarization R/G optotype 71 and the left polarization R/G optotype 73 is presented in black. In this case, the fusion optotype 75 is presented in white.

Also in the optotype presenting apparatus of the display type having the polarization optical member, the display 50 can be controlled to present the background region 77 of the right polarization R/G optotype 71 and the left polarization R/G optotype 73 in black, similarly to the case of the polarization red-green test chart presented by the optotype presenting apparatus of the projection type.

Figure 4:
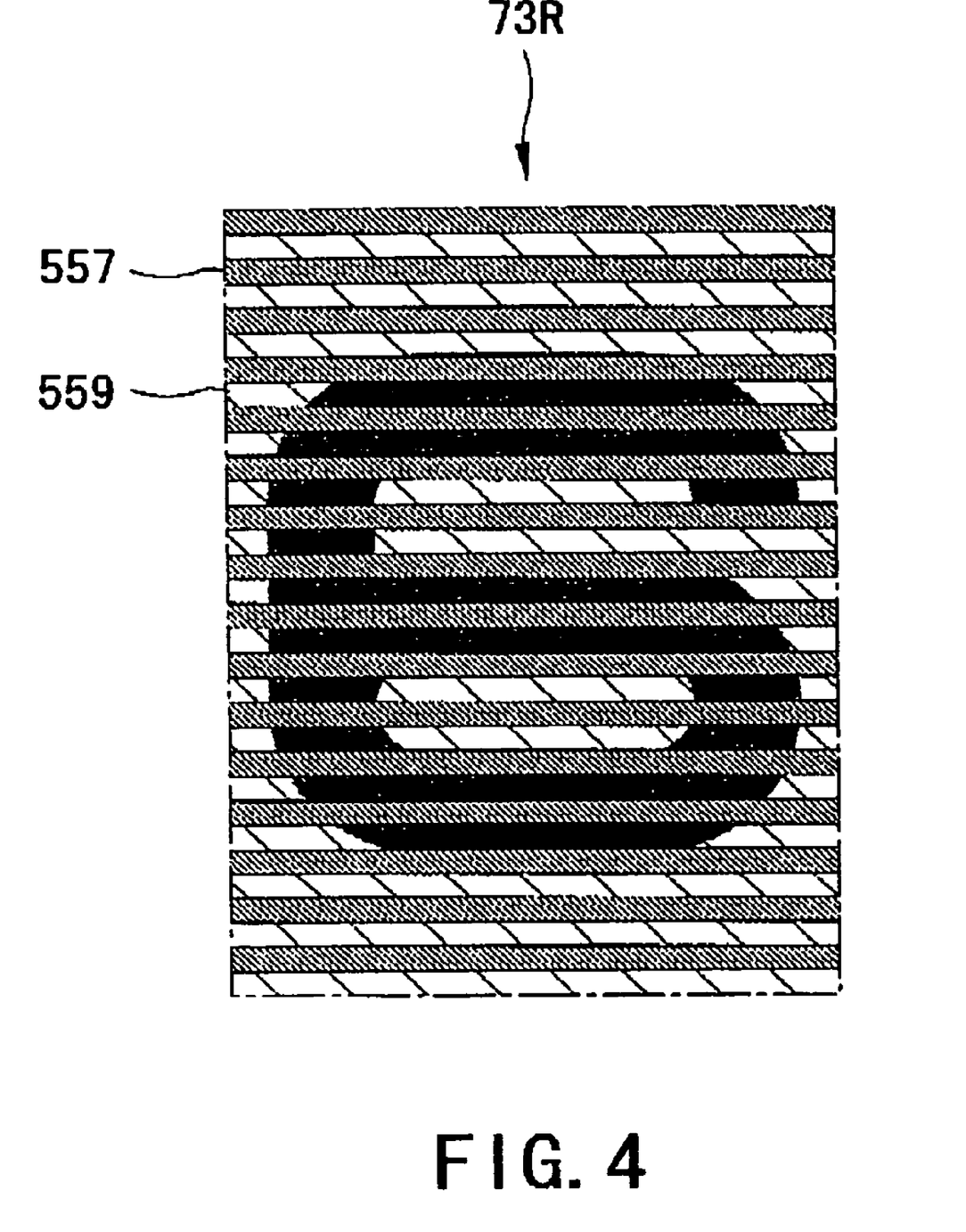
FIG. 4 is an enlarged view showing a red optotype in the polarization red-green test chart.

A description of the red optotype 73R presented by the presenting unit 3 in this case will be provided. FIG. 4 is an enlarged view of the red optotype 73R presented by the presenting unit 3. As shown in FIG. 4, the red optotype 73R in the left polarization R/G optotype 73 is arranged to be displayed only in the display regions 559 for the left eye by controlling the display 50. Since the red optotype 73R for the left eye should not be visually perceived by the right eye, the display 50 is controlled to display the display regions 557 for the right eye in black so that the optical regions 57 for the right eye to be presented to the right eye is visually perceived in black.

However, there is a gap albeit slightly between a liquid crystal element of the display 50 and the polarization optical member 55 placed in front of the liquid crystal element, so that the light exiting from the display regions 559 for the left eye leaks out and enters the optical regions 57 for the right eye of the polarization optical member 55 which are located at both adjacent sides (in a vertical direction) of the optical regions 59 for the left eye.

Here, a region corresponding to the rod optotype 73R in the polarization red-green test chart 70 is considered. Not only the light exiting from the display regions 557 enters the optical regions 57 for the right eye, but also a slight amount of the light exiting from the display regions 559 leaks out and enters the optical regions 57 for the right eye. In other words, the red light leaks out and enters the optical regions 57. Accordingly, the left polarization R/G optotype 73 is faintly visually perceived unintentionally in the region 73A in FIG. 3C, although the region 73A should be visually perceived in black. This is because red and green are visually perceived to be more conspicuous than black. Therefore, the left polarization R/G optotype 73 is faintly visually perceived unintentionally by the right eye through the polarization filter 30R even though the intensity of the red or green light is small in comparison with black displayed in the optical regions 57 for the right eye.

Similarly to the above case, also in the case of presenting the left polarization R/G optotype 73 to the left eye, the right polarization R/G optotype 71 is faintly visually perceived unintentionally by the left eye because of the light which leaks out and enters the optical regions 59, although the region 71A should be visually perceived in black only. In these cases, a test result obtained by using the polarization red-green test chart 70 is less reliable.

Figure 5A:
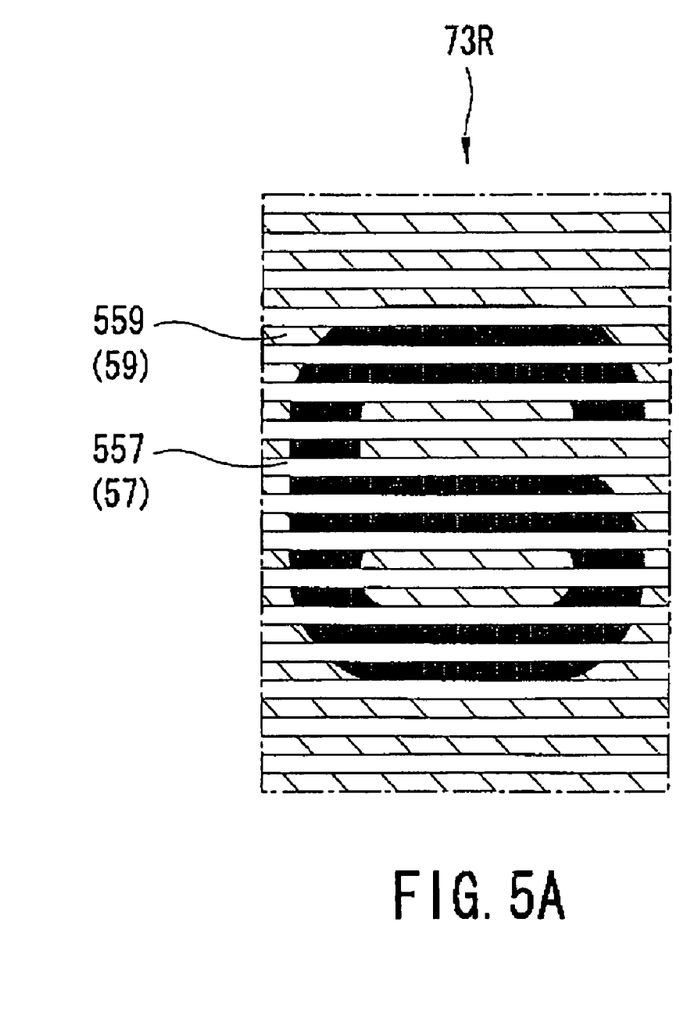
FIGS. 5A and 5B are enlarged views for illustrating how red optotypes in the polarization red-green test chart are presented.

Hereinafter, a description of a manner will be provided referring to FIGS. 5A and 5B, by which the optotype which is visually perceived unintentionally in the region where the optotype should not be visually perceived because of the light leaking out and entering the unintended optical regions as described above is arranged not to be visually perceived in the region as much as possible. FIG. 5A is an enlarged view showing the red optotype 73R presented by the presenting unit 3, which is similar to FIG. 4.

In FIG. 5A, the red optotype 73R in the left polarization R/G optotype 73 is arranged to be displayed only in the display regions 559 for the left eye by controlling the display 50. The red optotype 73R for the left eye should not be visually perceived by the right eye. Hence, in order that the red optotype 73R for the left eye is not visually perceived by the right eye, the display 50 is controlled to display the display regions 557 for the right eye in white so that the optical regions 57 for the right eye to be presented to the right eye are visually perceived in white in contrast to black in FIG. 4. The green optotype 73G for the left eye is also arranged similarly by controlling the display 50, so that a detailed description of the green optotype 73G is omitted.

Figure 5B:
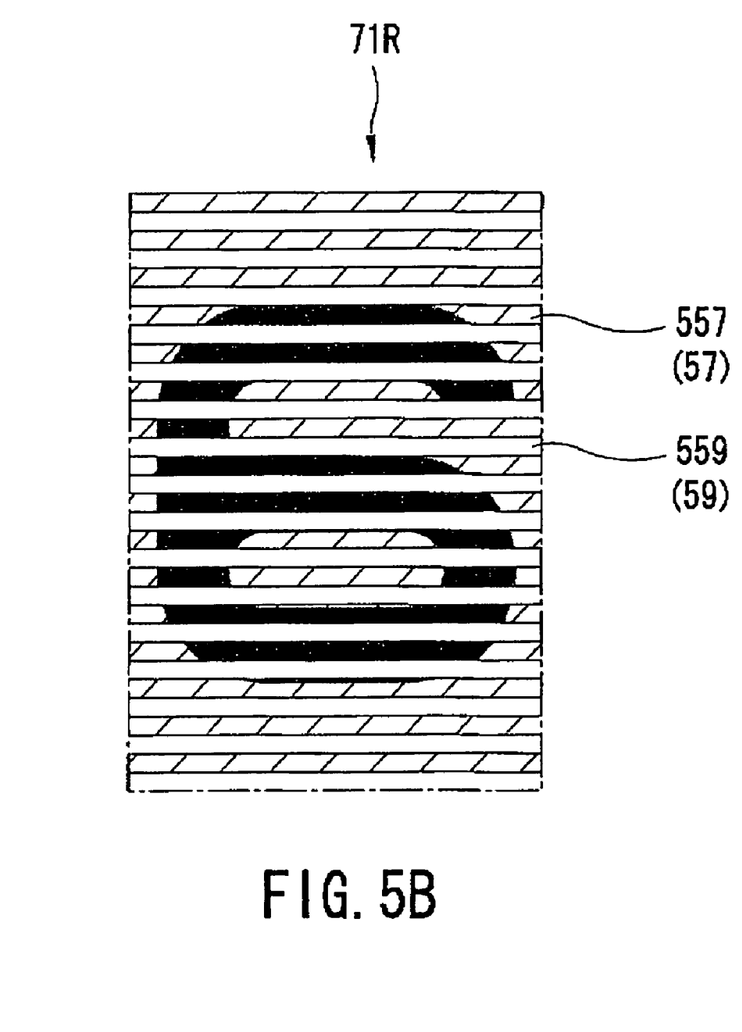

In addition, a description of the red optotype 71R to be presented to the right eye will be provided referring to FIG. 5B. The red optotype 71R in the right polarization R/G optotype 71 is arranged to be displayed only in the display regions 557 for the right eye by controlling the display 50. The red optotype 71R for the right eye should not be visually perceived by the left eye. Hence, in order that the red optotype 71R for the right eye is not visually perceived by the left eye, the display 50 is controlled to display the display regions 559 for the left eye in white so that the optical regions 59 for the left eye to be presented to the left eye are visually perceived in white. The green optotype 71G for the right eye is arranged similarly by controlling the display 50, so that a detailed description of the green optotype 71G is omitted. The display 50 is controlled to display the background region 77 of the right polarization R/G optotype 71 and the left polarization R/G optotype 73 also in white.

Figure 6A:
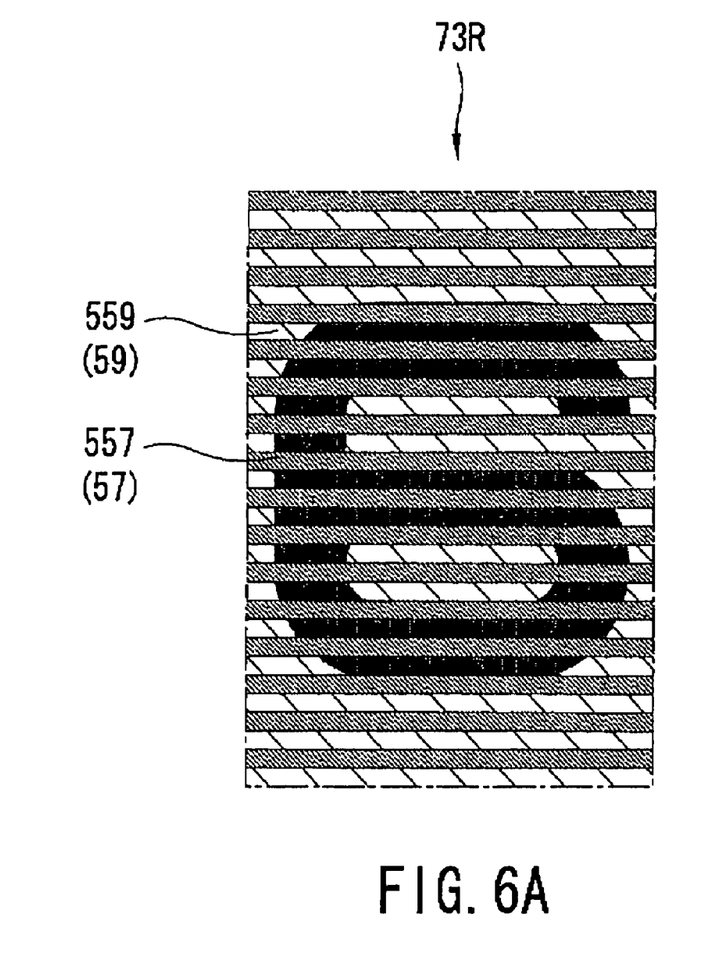
FIGS. 6A and 6B are enlarged views for illustrating how the red optotype is visually perceived.
Figure 6B:
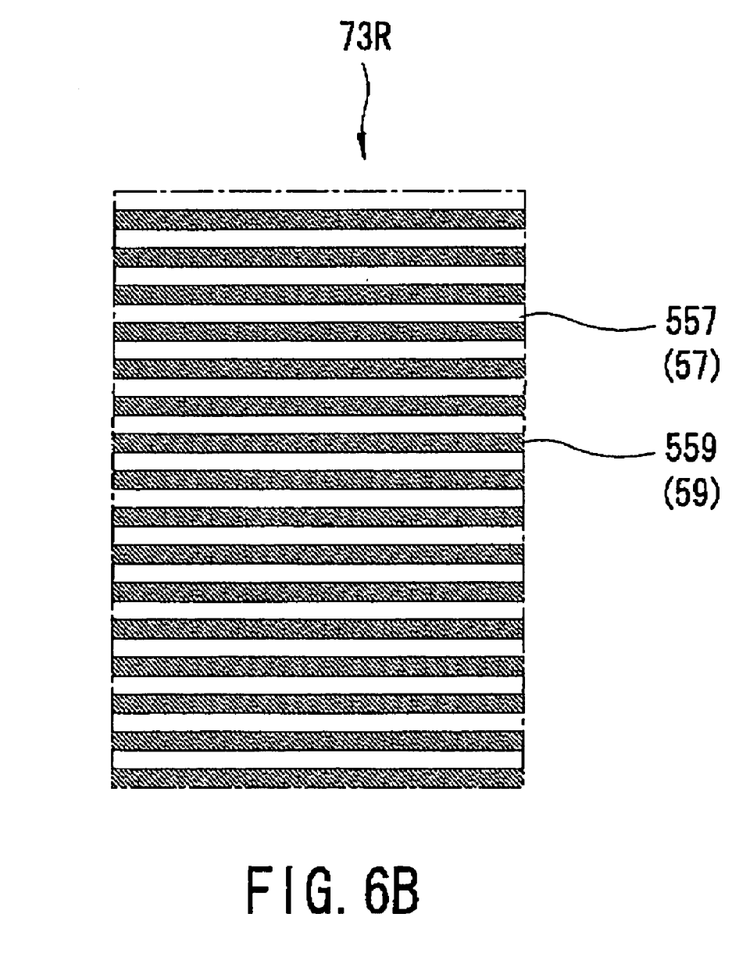

FIG. 6A is a view showing how the red optotype 73R in the left Polarization R/G optotype 73 is visually perceived by the left eye through the polarization filter 30L, and FIG. 6B is a view showing how the red optotype 73R in the left polarization R/G optotype 73 is visually perceived by the right eye through the polarization filter 30R.

The light of the red optotype 73R which passed through the polarization filter 30L via the optical regions 59 reaches the left eye. Meanwhile the white light which exits from the optical regions 57 is blocked by the polarization filter 30L because the white light cannot pass through the polarization filter 30L of which the polarizing axis is perpendicular to that of the white light. Accordingly, the black optical regions 57 and the light of the red optotype 73R which exits from the optical regions 59 are alternately presented as shown in FIG. 6A, so that the left polarization R/G optotype 73 is visually perceived by the left eye (i.e., the red optotype 73R is perceived in red by human eyes because the light of the red optotype 73R is brighter than the black optical regions 57).

On the other hand, the light of the red optotype 73R which exits from the optical regions 59 is blocked by the polarization filter 30R because the light cannot pass through the polarization filter 30R of which the polarizing axis is perpendicular to that of the light. Meanwhile the white light which exits from the optical regions 57 reaches the right eye because the white light can pass through the polarization filter 30R of which the polarizing axis is in the same direction as that of the white light. Accordingly, the white light which exits from the optical regions 57 and the black optical regions 59 are alternately presented as shown in FIG. 6B, so that the region 73A is visually perceived in white by the right eye since the white light is far brighter than black (the same can be said to the background region 77). Incidentally, in the preferred embodiment of the present invention, the word "white" indicates substantially white color, and it should be understood that the word is not meant to indicate white in chromaticity coordinates.

Similarly to the case described referring to FIG. 4, not only the light exiting from the display regions 557 for the right eye of the display 50 enters the optical regions 57 for the right eye, but also the light exiting from the display regions 559 for the left eye leaks out and enters the optical regions 57 for the right eye. In other words, not only the white light (a major part of the light which enters the optical regions 57 for the right eye) which should by itself enter the optical regions 57 for the right eye, but also the leaked light of the red optotype 73R unintentionally enters the optical regions 57 for the right eye. However, since human eyes have the property of visually perceiving white more easily than red or green in addition to the property of visually perceiving red or green more easily than black, red light or green light which leaks out and enters the optical regions 57 for the right eye is extremely hard to be visually perceived. By such properties, the right polarization R/G optotype 71 and the fusion optotype 75 are visually perceived by the right eye via the polarization filter 30R, while the region 73A where the left polarization R/G optotype 73 is placed is visually perceived in white which is the same color as the background region 77, as shown in FIG. 3C. Similarly, the left polarization R/G optotype 73 and the fusion optotype 75 are visually perceived by the left eye via the polarization filter 30L, while the region 71A where the right polarization R/G optotype 71 is placed is visually perceived in white which is the same color as the background region 77, as shown in FIG. 3B.

Incidentally, in the preferred embodiment of the present invention, the fusion optotype 75 is made black; however, the color of the fusion optotype 75 is not limited to black and any color may be preferably used only if the color of the fusion optotype 75 is different from and is in clear contrast with the color of the background region 77.

As described above, since the display 50 is controlled to display also the background region 77 in white, the problem that the optotype which should not be visually perceived is faintly visually perceived unintentionally can be solved as much as possible, which therefore allows a polarization red-green test with accuracy to be performed. In other words, a binocular balance test to check a difference between vision of the right eye and vision of the left eye can be performed by comparing how the right polarization R/G optotype 71 and the left polarization R/G optotype 73 are visually perceived by the right eye and the left eye, and concurrently, a red-green test to check whether the corrected refractive power of the right eye and the left eye is undercorrection or overcorrection can be performed.

Incidentally, the fusion optotype 75 is not an essential constituent element. However, if the right polarization R/G optotype 71 and the left polarization R/G optotype 73 are visually perceived to be apart due to heterophoria in the binocular balance test, the comparison how the right polarization R/G optotype 71 and the left polarization R/G optotype 73 are visually perceived by the right eye and the left eye is hard to be made, so that it is preferable for the fusion optotype 75 to be included in order to align the optotypes 71 and 73 and make them easy to visually perceive.

Incidentally, the placement of the right polarization R/G optotype 71 and the left polarization R/G optotype 73 in the polarization red-green test chart 70 is not limited to the placement shown in FIGS. 3A to 3C. The placement shown in FIGS. 7A to 7C, or other types of placement is also preferably used.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as is suited to the particular use contemplated. It is intended that the scope of the invention be defined by the claims appended hereto, and their equivalents.

What is claimed is:

1. An optotype presenting apparatus which presents an optotype and a test chart used for testing visual performance, the apparatus comprising:
   a display;
   a polarization optical member placed in front of the display, which includes first optical regions and second optical regions which are alternately arranged in either one of a linear pattern and a grid pattern based on the size of pixels of the display, the first optical regions changing light exiting from the display into light having a polarizing axis, the second optical regions changing light exiting from the display into light having a polarizing axis, the polarizing axes being perpendicular to each other;

a selector which comprises a switch with which a test chart for a binocular visual test including a polarization red-green test chart is selected;

a region where an optotype for a left eye is to be presented and a region where an optotype for a right eye is to be presented, the regions being provided on a display surface of the display; and a controller which controls display of the display, wherein, when the polarization red-green test chart is selected with the selector, the controller controls the display to display a polarization red-green optotype for a left eye in pixel regions which correspond to the first optical regions and are within the region where the optotype for the left eye is to be presented, and controls the display to display pixel regions in white which correspond to the second optical regions and are within the region where the optotype for the left eye is to be presented, while the controller controls the display to display a polarization red-green optotype for a right eye in pixel regions which correspond to the second optical regions and are within the region where the optotype for the right eye is to be presented, and controls the display to display pixel regions in white which correspond to the first optical regions and are within the region where the optotype for the right eye is to be presented.

2. The optotype presenting apparatus according to claim 1, further comprising a region where a fusion optotype is to be presented, which is provided on the display surface of the display, wherein the controller controls the display to display fusion optotypes, which have substantially the same shape and the same predetermined easily perceived color, individually in pixel regions which correspond to the first optical regions and in the second optical regions.

3. The optotype presenting apparatus according to claim 1, further comprising a background region for the polarization red-green test chart, which is provided on the display surface of the display, wherein the controller controls the display to display pixel regions which correspond to the first optical regions in white which are in a background region for the polarization red-green optotype for the left eye, and controls the display to display pixel regions which correspond to the second optical regions in white which are in a background region for the polarization red-green optotype for the right eye.

4. The optotype presenting apparatus according to claim 1, wherein the display is a liquid crystal display.

5. The optotype presenting apparatus according to claim 1, wherein the light which exits from the display does not have a property of linearly polarized light, the apparatus further comprising a polarization plate which is placed between the display and the polarization optical member.

6. The optotype presenting apparatus according to claim 1, wherein the light which exits from the display does not have a property of linearly polarized light, and the polarization optical member is polarization plates having polarizing axes perpendicular to each other, the apparatus further comprising a polarization plate which is placed between the display and the polarization optical member.

* * * * *